United States Patent
Haider

(10) Patent No.: US 7,084,644 B2
(45) Date of Patent: Aug. 1, 2006

(54) CIRCUIT ARRANGEMENT FOR CAPACITIVE HUMIDITY MEASUREMENT AND METHOD FOR OPERATING THE SAME

(75) Inventor: Albin Haider, Linz (AT)

(73) Assignee: E+E Elektronik Ges.m.b.H., Engerwitzdorf (AT)

( * ) Notice: Subject to any disclaimer, the term of this patent is extended or adjusted under 35 U.S.C. 154(b) by 0 days.

(21) Appl. No.: 11/050,080

(22) Filed: Feb. 2, 2005

(65) Prior Publication Data

US 2005/0174129 A1 Aug. 11, 2005

(30) Foreign Application Priority Data

Feb. 6, 2004 (DE) .................. 10 2004 006 020

(51) Int. Cl.
*G01R 27/26* (2006.01)
(52) U.S. Cl. .................. 324/664; 324/678
(58) Field of Classification Search ............... 324/664, 324/665, 678
See application file for complete search history.

(56) References Cited

U.S. PATENT DOCUMENTS

| | | | | |
|---|---|---|---|---|
| 4,282,480 | A * | 8/1981 | Fujito et al. | 324/665 |
| 4,431,962 | A * | 2/1984 | Kompelien | 324/664 |
| 5,146,412 | A | 9/1992 | Jones | |
| 2003/0010119 | A1 | 1/2003 | Toyoda | |
| 2004/0051396 | A1 | 3/2004 | Supper et al. | |
| 2005/0104604 | A1* | 5/2005 | Mellert et al. | 324/678 |

FOREIGN PATENT DOCUMENTS

| | | |
|---|---|---|
| DE | 41 03 433 A1 | 8/1991 |
| DE | 197 01 899 A1 | 10/1997 |
| EP | 1 341 306 A1 | 9/2003 |

OTHER PUBLICATIONS

Lutz Bierl, "Economic Measurement Techniques with the Comparator A Module," Texas Instruments Application Report SLAA071, published by Texas Instruments, Oct. 1999, pp. 1 and 26.
Dietz, Paul H. et al., "Wireless Liquid Level Sensing for Restaurant Applications," Proceedings of IEEE Sensors 2002, Orlando, Florida, vol. 1, of 2, Conf. 2, Jun. 12, 2002, pp. 715-720.

\* cited by examiner

Primary Examiner—Vincent Q. Nguyen
(74) Attorney, Agent, or Firm—Brinks Hofer Gilson & Lione

(57) ABSTRACT

A circuit arrangement for capacitive humidity measurement that includes a capacitive element to be measured, a plurality of switch elements, a charge storage element and a control unit electrically connected to the capacitive element, the plurality of switch elements and the charge storage element. The control unit controls the plurality of switch elements so that a number of charging operations and a number of discharging operations of the capacitive element are performed, as well as a parallel charging of the charge storage element takes place, until the charge storage element has been charged to a defined reference value, and a determination of a capacitance of the capacitive element is performed from a determination of the number of charging operations, or of a time until the reference value is reached.

35 Claims, 5 Drawing Sheets

CIRCUIT ARRANGEMENT FOR CAPACITIVE HUMIDITY MEASUREMENT AND METHOD FOR OPERATING THE SAME

Applicant claims, under 35 U.S.C. § 119, the benefit of priority of the filing date of Feb. 6, 2004 of a German patent application, copy attached, Ser. No. 10 2004 006 020.7, filed on the aforementioned date, the entire contents of which is incorporated herein by reference

BACKGROUND OF THE INVENTION

1. Field of the Invention

The present invention relates to a circuit arrangement for capacitive humidity measurement, including at least one capacitive element to be measured, several switch elements, at least one charge storage element, as well as a control unit. The present invention furthermore relates to a method for operating a circuit arrangement for capacitive humidity measurement.

2. Discussion of Related Art

In connection with various applications, there exists today a requirement for the exact monitoring of defined ambient conditions and, if required, their control within a predetermined range. This can be the case, for example, in connection with modern production processes, in the air-conditioning technology, in the field of motor vehicles, or even with household appliances. Besides monitoring and regulating the temperature as the most important ambient parameter, it has become increasingly necessary to also monitor and, if required, regulate the ambient humidity.

Capacitive humidity sensors are often employed on the part of the sensor, which are mostly produced by thin film technology. Customarily, capacitive humidity sensors include two oppositely located flat metal electrodes, between which a hygroscopic material, customarily a polymer, is arranged. The polymer has a humidity-dependent dielectric constant, so that in accordance with measuring technology a plate capacitor results in the end, whose capacitance changes as a function of the relative ambient humidity. Therefore the respective actual capacitance of the humidity sensor functions as the measuring value of the relative humidity. Various measuring methods are used for measuring the capacitance of capacitive humidity sensors.

For example, it is known from DE 41 03 433 A1 to base the capacitance measurement on a frequency measurement in an LC- or RC-oscillating circuit, wherein the measured frequency again changes as a function of the oscillating circuit, and therefore of the relative humidity. Besides the multitude of required structural components for constructing the respective oscillating circuit, as a disadvantage of this variation it must also be noted that it also has a comparatively large electrical current consumption. Added to this is that, for an exact frequency measurement, which does not change even under fluctuating ambient conditions, nor over the course of the operating time, a stable time base is required. These requirements cannot be assured in a simple manner.

Alternatively to this it is known to perform the required capacitance measurement in a capacitive humidity sensor by means of a time measurement. An appropriate circuit is known, for example, from the Application Report SLAA071 (October 1999) of Texas Instruments with the title "Economic Measuring Techniques with a Comparator-A Module (L. Bierl), p. 26 (item 2.7). The charging time required for charging the measuring capacitors to a predetermined voltage is determined by such a process. For measuring small capacitances (C <200 pF) in particular, however, a high chronological resolution of the measurement is required. If the required high resolution of the time measurement is not available, very large resistance values (>1 MΩ) are alternatively required in the respective circuit. In turn, this has negative effects on the stability of the circuit in respect to fluctuating soiling or humidity. Moreover, such interferences can lead to false measurements, since in the course of the measurement a small charge actually is moved only once. If a possible interference results at exactly that time, an erroneous capacitance determination can be the result of this.

OBJECT AND SUMMARY OF THE INVENTION

It is an object of the present invention to disclose a circuit arrangement for capacitive humidity measurement, as well as a method for operating it. It is intended in this connection to assure a dependable measuring operation with the least possible outlay.

This object is attained by a circuit arrangement for capacitive humidity measurement that includes a capacitive element to be measured, a plurality of switch elements, a charge storage element and a control unit electrically connected to the capacitive element, the plurality of switch elements and the charge storage element. The control unit controls the plurality of switch elements so that a number of charging operations and a number of discharging operations of the capacitive element are performed, as well as a parallel charging of the charge storage element takes place, until the charge storage element has been charged to a defined reference value, and a determination of a capacitance of the capacitive element is performed from a determination of the number of charging operations, or of a time until the reference value is reached.

The stated object is further attained by a method for operating a circuit arrangement for capacitive humidity measurement, which is comprised of a capacitive element, a plurality of switch elements, a charge storage element and a control unit. The method includes performing charging and discharging of the capacitive element via the plurality of switch elements and the control unit and performing parallel charging of the charge storage element via the plurality of switch elements and the control unit. The charging and discharging of the capacitive element and the parallel charging are performed until the charge storage element has been charged to a defined reference value. Performing a definition of a capacitance of the capacitive element by determining either a number of charging operations, or of a time until the reference value is reached.

In accordance with the present invention, the capacitive element to be measured and a charge storage element are charged in parallel, and thereafter only the capacitive element is discharged. It is assured in the course of the discharge operation that no discharge of the charge storage element takes place. This is repeated until the charge in the charge storage element, or the voltage in the charge storage element, exceeds a predetermined reference value. The capacitance of the capacitive element to be measured is then calculated from the number of charge operations performed up to that time, or from the time until the reference value has been reached.

In an advantageous embodiment, the circuit arrangement in accordance with the present invention contains two capacitive elements to be measured, namely a capacitive humidity sensor element, as well as a capacitive reference element of known capacitance. The determination of the capacitance of interest of the humidity sensor element can be performed by two measurements, in which the two capacitive elements are cyclically charged and discharged as explained above, and the respective number of such cycles, or the elapsed time until the reference value is reached, is determined. The capacitance of the humidity sensor element, which in turn has an approximate linear connection with the wanted measured value, i.e. the relative humidity, results in a simple manner in connection with the known capacitance of the reference element.

The attainment of the object in accordance with the present invention has been shown to be particularly advantageous because of the small number of required structural elements. Added to this is that the capacitance measurement of the reference element, as well as of the humidity sensor element, can be performed with the almost identical structural components. This means that possible changes in the supply voltage, the electrical input currents, etc., always act on both separate measurements equally and therefore can be eliminated. An increased accuracy of the measurements results from this.

Further advantages, as well as details, of the present invention ensue from the following description of exemplary embodiments by the attached drawings.

DETAILED DESCRIPTION OF THE PREFERRED EMBODIMENTS

Figure 1:
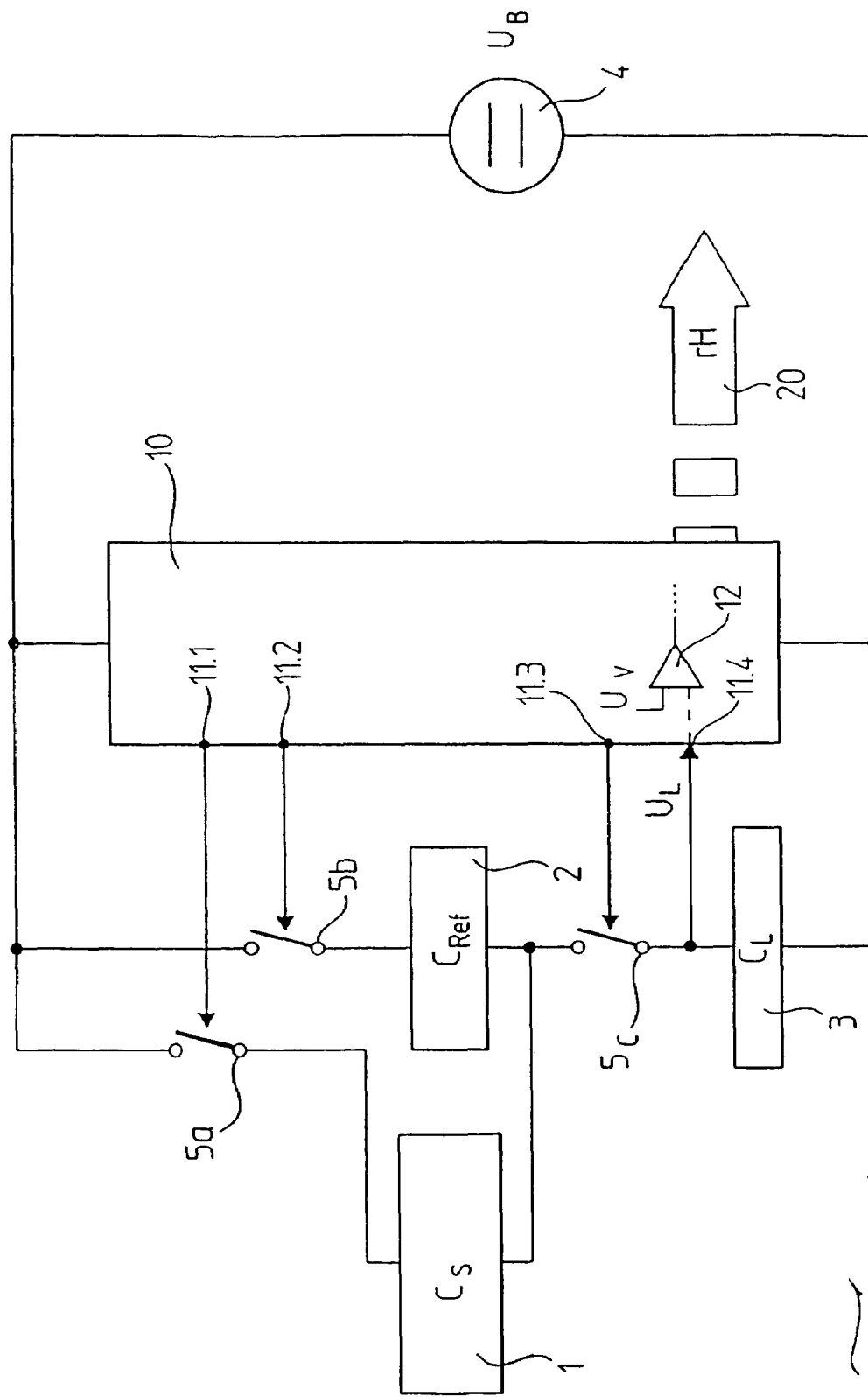
FIG. 1 is a greatly schematized block circuit diagram of an embodiment of a circuit arrangement in accordance with the present invention.

A greatly schematized block circuit diagram of a possible embodiment of the circuit arrangement for capacitive humidity measuring in accordance with the present invention is represented in FIG. 1.

The embodiment of the circuit arrangement includes two capacitive elements 1, 2, of which a first element 1 is designed as a capacitive humidity sensor element, and a second element 2 as a capacitive reference element. Here, the humidity sensor element 1 is constructed in a known manner and, as explained at the outset, includes two metal electrodes, between which a humidity-sensitive polymer material is arranged, wherein the entire structure is arranged on a glass support substrate. Suitable capacitive humidity sensor elements 1 are sold by Applicant, E+E Elektronik Ges.m.b.H. of Engerwitzdorf, Austria identified, as Types HC101, HC103 or HC104, for example.

As already explained at the outset, the capacitive humidity sensor element 1 has a capacitance $C_S$ as the electrical value to be measured. The capacitance $C_S$ changes in a defined manner as a function of the ambient humidity rH. For example, at a relative ambient humidity rH=0%, the capacitance $C_S \approx 160$ pF, and at a relative ambient humidity rH=76%, the capacitance $C_S \approx 202$ pF. Therefore, with an approximately assumed linear connection of the values $C_S$ and rH, the capacitance $C_S \approx 215$ pF at a relative ambient humidity rH=100%.

The reference element 2 is embodied as a commercially available capacitor, for example as an NPO capacitor, and has the known capacitance $C_{Ref}$, for example $C_{Ref}=180$ pF. Because of the customarily provided calibration of the entire system at a defined humidity, the exact knowledge of $C_{Ref}$ is not of primary importance in the selection of a suitable reference element 2. It need merely be assured that the reference element 2 remains stable during the measuring operation in respect to fluctuations in the temperature, the voltage, the operating time, etc.

The circuit arrangement in accordance with the invention furthermore includes a charge storage element 3, which is also embodied in the form of a capacitor and has a capacitance $C_L=1$ μF, for example. Preferably the capacitance of the charge storage device 3 is selected to be clearly greater than the capacitance $C_{Ref}$ of the reference element 2, i.e. $C_L>>C_{Ref}$, in order to achieve a sufficient resolution in the course of the capacitance measurement. In this way the ratio $C_L/C_{Ref}$ is a measure of the resolution of the capacitance measurement in accordance with the present invention. Accordingly, the greater this ratio is selected to be, the greater the available measurement resolution. During the actual measurement it must be assured that the capacitance $C_L$ of the charge storage element 3 does not possibly change. For this purpose, the leakage current and the value of the capacitance $C_L$ of the charge storage element 3 must be as low as possible over the entire operating temperature, so that in case of a more rapid temperature change the leakage current does not change between the measurement with the humidity sensor element 1 and the measurement with the reference element 2.

The charge storage element 3 can be selectively connected in series with one of the two capacitive elements 1, 2 via various switch elements 5a, 5b, 5c, moreover, in the open state the switch element 5c is used to prevent a discharge of the charge storage element 3 during a defined measurement phase.

The switch elements 5a, 5b, 5c are controlled in the desired manner via different outputs 11.1, 11.2, 11.3 of the control unit and are brought into the respectively required position.

In the present example, the different switch elements 5a, 5b, 5c can each take up three switching states I, II, III in principle, namely switching state I=switch element closed,
switching state II=switch element open, as well as
switching state III=switch element open and grounded (GND=−$U_B$).

In FIG. 1, the three switch elements 5a, 5b, 5c are each in the switching state II.

Regarding the actual design of the switch elements 5a, 5b, 5c, there are of course various options besides the indicated realization in the form of discrete structural components. Thus, they can be designed in an integrated form together with the further components of the circuit arrangement in accordance with the present invention. Moreover, the switch elements 5a, 5b can already be contained in the control unit or the microprocessor as software and/or hardware. The switch element 5c, which is primarily intended to prevent the discharge of the charge storage element 3 during the discharge of the other two elements 1 and 2, can furthermore also be designed as a diode. The representation of the switch elements 5a, 5b, 5c in the drawings as actual switches was primarily selected for reasons of improved understanding of the method to be explained in what follows.

Furthermore, a control unit 10, which is preferably embodied as a microprocessor and inter alia has a number of definitely switchable inputs and outputs, or ports 11.1 to 11.4, is relevant to the functioning of the circuit arrangement in accordance with the present invention, or of the method in accordance with the present invention. The various inputs and outputs 11.1 to 11.4 of the control unit 10 are connected in the manner shown with the switch elements 5a, 5b, 5c, as well as with a voltage pickup above the charge storage element 3. Reference is made to the following explanation of the method in accordance with the invention regarding the functioning or control of the various switch elements 5a, 5b, 5c.

The control unit 10 furthermore includes an internal comparator unit 12, which has two inputs and is connected with the input 11.4. A measuring voltage $U_L$ has been applied to a first input of the comparator unit 12, which corresponds to the voltage above the charge storage element 3, and a predetermined comparison voltage $U_V$ has been applied to the second input. In a possible exemplary embodiment, the comparison voltage $U_V$ is selected to be $U_V$=2.5 V. Furthermore, regarding the comparison voltage $U_V$, its size is less important than its stability, or constancy, during the course of the measurement. The function of the comparator unit 12 will also be addressed in greater detail in the course of the subsequent description.

The electrical current or voltage supply of the circuit arrangement in accordance with the present invention is provided via a schematically indicated power supply 4. The latter supplies an operating voltage $U_B$ (for example between 2.3 V and 5.5 V), with which the control unit 10 is supplied, and with which the charging of the various capacitive elements 1, 2, as well as of the charge storage element 3, is provided within the framework of the method in accordance with the present invention. In one exemplary embodiment, $U_B$ is selected to be 5 V, for example, the comparison voltage $U_V$ then is 2.5 V, as mentioned above.

In connection with the control unit 10, an output 20 is furthermore schematically indicated, at which the measurement value of interest in the end, i.e. the detected relative humidity rH, is available in digital form for further processing.

In principle, the capacitance $C_S$ of the capacitive humidity sensor element 1, as well as the capacitance $C_{Ref}$ of the capacitive reference element 2, can be separately determined with the circuit arrangement shown. In what follows, the determination of the capacitance $C_S$ of the humidity sensor element 1 will be described by way of example.

Figure 2A:
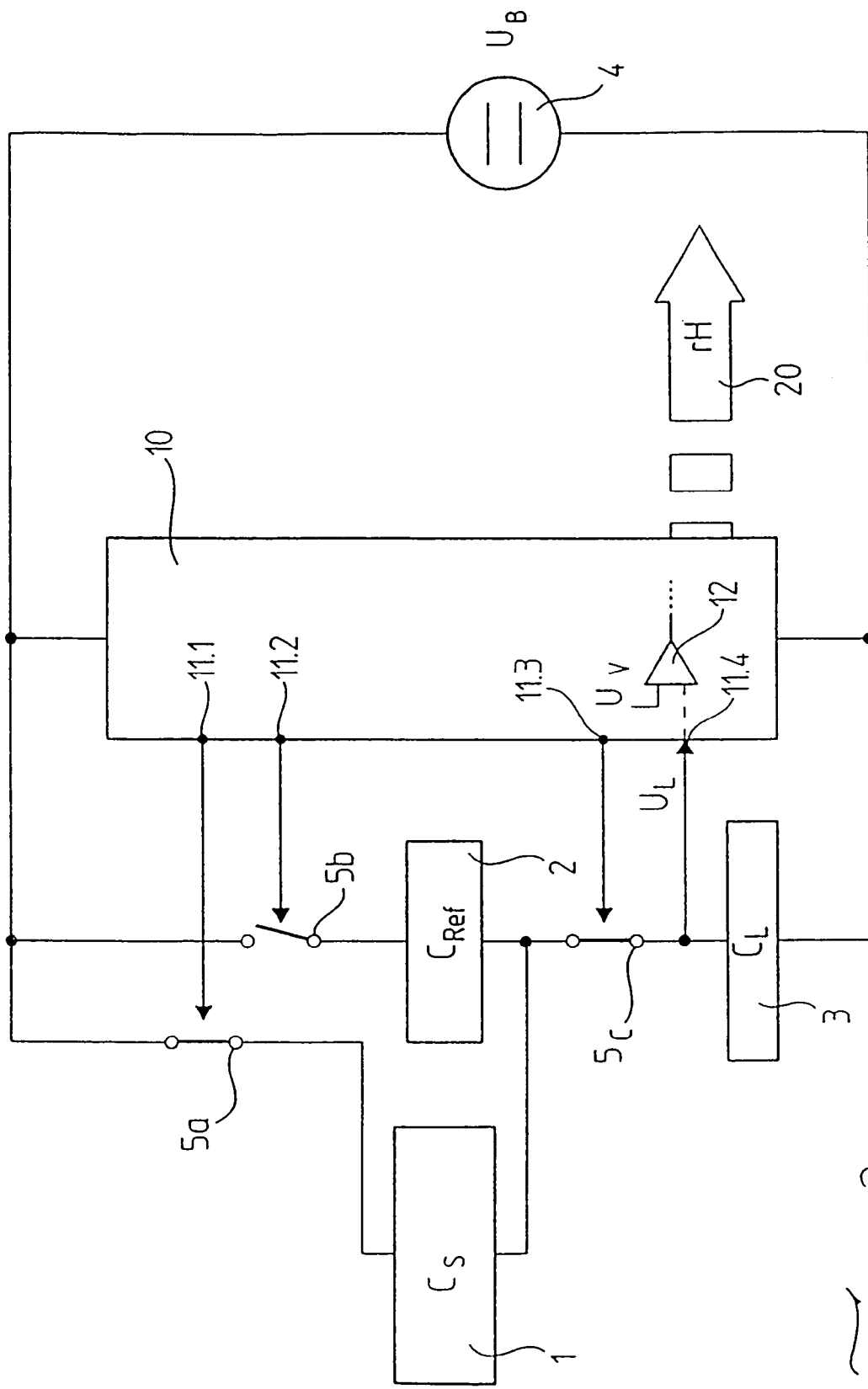
FIGS. 2a and 2b each represent a block circuit diagram of the circuit arrangement of FIG. 1 in accordance with the present invention during different phases of the separate reference element measurement.

It must be assured prior to the start of the capacitance determination that all existing capacitances $C_S$, $C_{Ref}$, $C_L$ in the circuit arrangement in accordance with the invention are discharged as completely as possible. For the actual measurement, in a first charging operation the humidity sensor element 1 is initially switched in series with the charge storage device 3 via the various switch elements 5a, 5b, 5c, and the humidity sensor element 1, as well as the charge storage element 3, are charged to a defined charge value Qn. The switching state of the various switch elements 5a, 5b, 5c in this measurement phase required for this is represented in FIG. 2a. While the switch element 5b remains open (switching state II) via the output 11.2 of the control unit 10 in order to prevent the charging of the reference element 2, the switch elements 5a, 5c remain closed (switching state I), controlled via the outputs 11.1, 11.3.

Here, the charge value Qn applied to the capacitors during this charging operation results in principle from $$Qn = C*dU \qquad \text{(Equ. 1)}$$

wherein:
C=the capacitance of the humidity sensor element/charge storage element
dU=voltage at the humidity sensor element/charge storage element If it is assumed that all capacitances or capacitors of the arrangement had been fully discharged prior to the first charging operation, the charge Qn applied to the humidity sensor element 1 is approximately as follows:

$$Qn = C_S*dU_S = C_S*U_S = C_S*(U_B - U_D - U_L) \qquad \text{(Equ. 2)},$$

wherein:
$C_S$=capacitance of the humidity sensor element 1
$U_S$=voltage at the humidity sensor element 1
$U_B$=operating voltage of the power supply 4
$U_D$=voltage at switch element 5c
$U_L$=voltage at the charge storage element 3.

On the basis of the exemplary values of $C_S$=180 pF, $U_B$=5.0 V, $U_D$=0.3 V, $U_L$=0.0 V for the first charging operation, Qn is determined to be 846 pC. If, as explained, this charge amount is also applied to the charge storage element 3, a voltage rise $dU_L$ results there in accordance with $$dU_L = Qn/C_L = 846 \text{pC}/1 \mu F = 0.846 \text{ mV}.$$

Figure 2B:
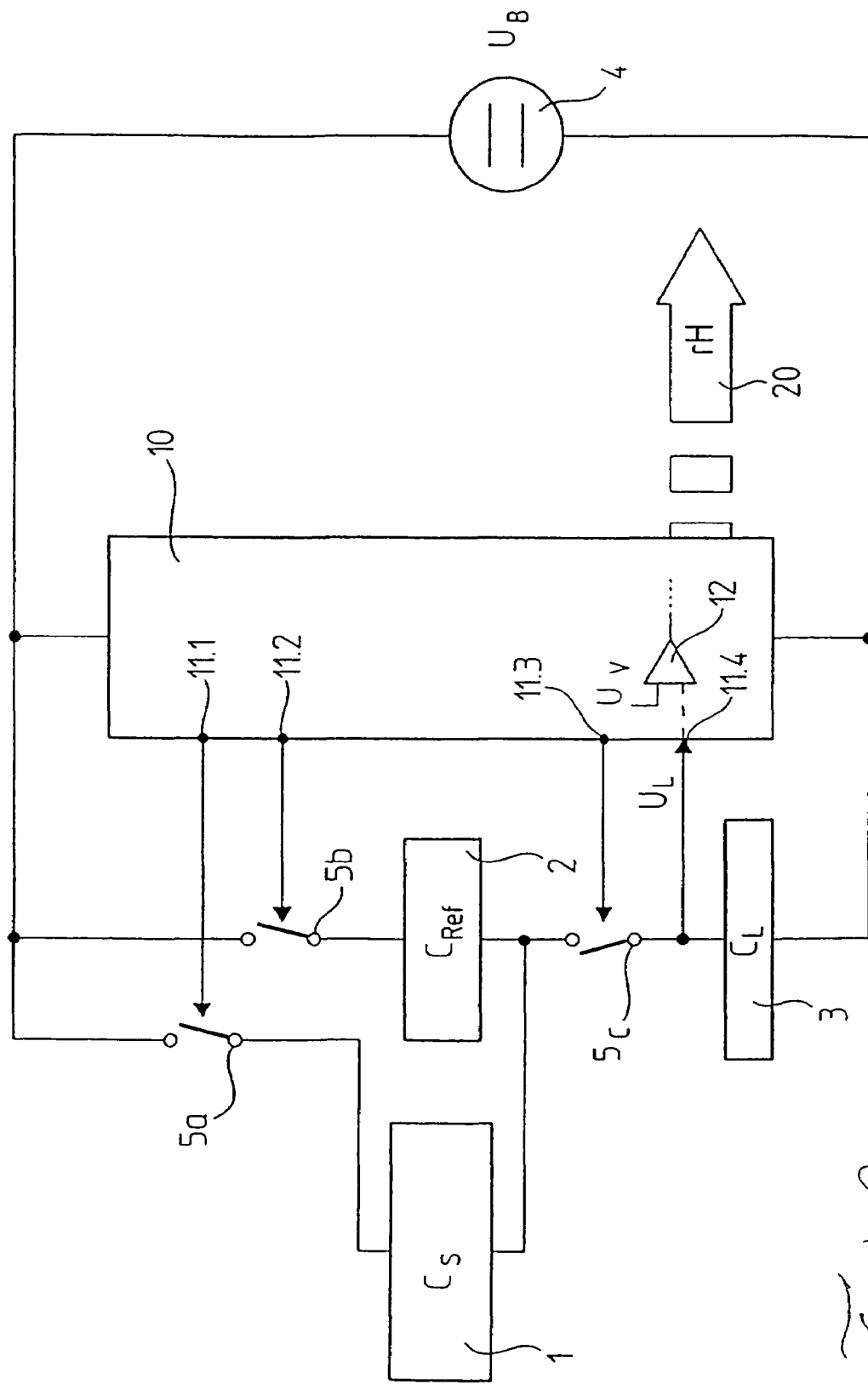
Figure 2C:
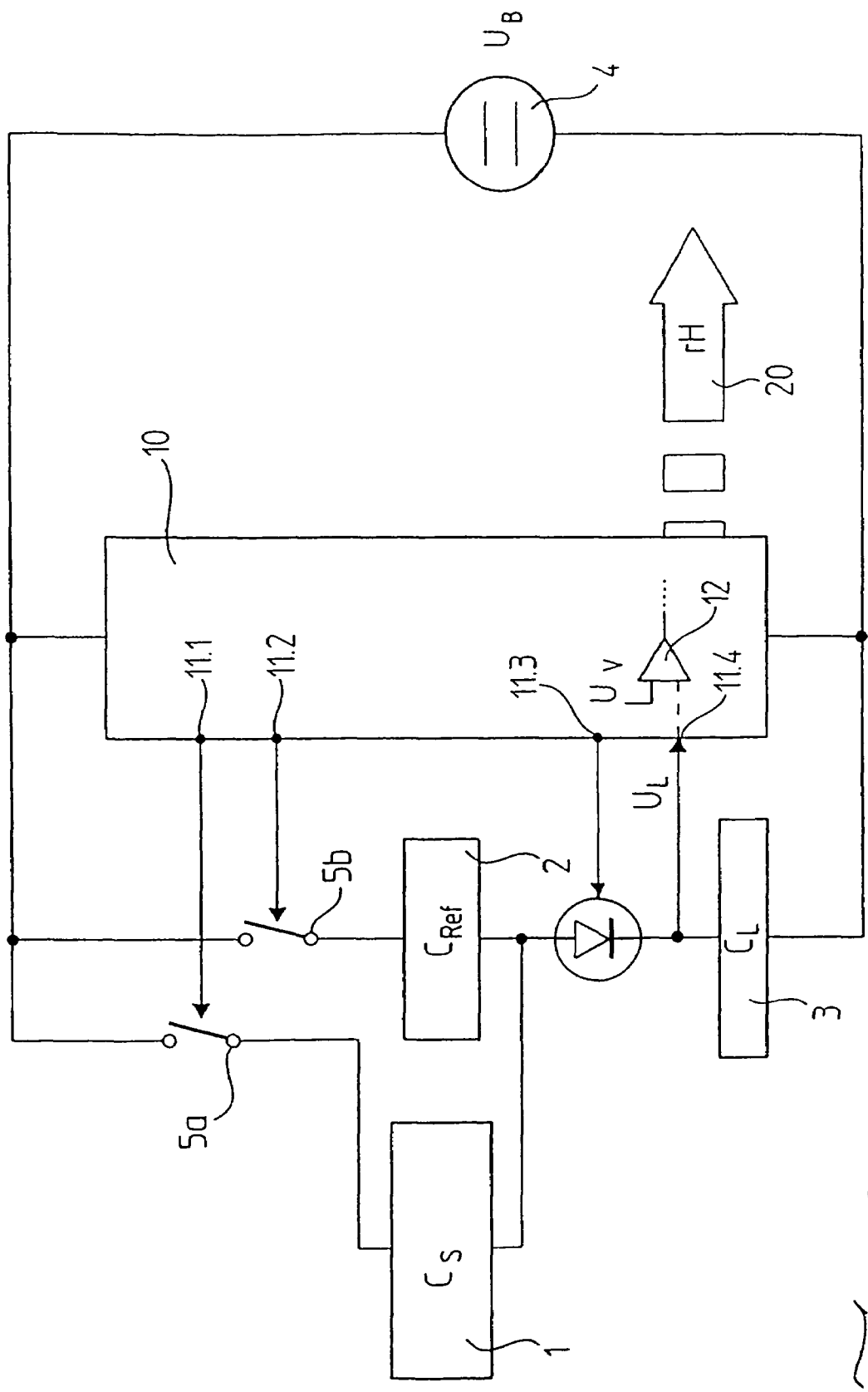
FIG. 2c represents a block circuit diagram of a variation of the circuit arrangement of FIG. 1 in accordance with the present invention during a phase of the separate reference element measurement.

In the subsequent method step only the capacitive humidity sensor element is completely discharged, while it is prevented by the switch element 5c that a discharge of the charge storage element 3 occurs simultaneously. The corresponding state of the various switch elements 5a, 5b, 5c during this measurement phase is represented in FIG. 2b. While the switch element 5b again remains open in the switching state II, in contrast to the previous measurement phase now the switch element 5a is triggered via the output 11.1 and is in the switched phase III for discharging the humidity sensor element 1. But the switch element 5c is in the switching state II and is open, so that a discharge of the charge storage element 3 is prevented. As already indicated above, the function of the switch element 5c can also be realized by a diode suitably arranged at this location as shown in FIG. 2c.

In connection with the discharge of the humidity sensor element 1 it must be assured that the voltage at the humidity sensor element 1 does not exceed the supply voltage $U_B$, or does not drop below the value GND, so that the control unit 10 is not possibly damaged. This can be assured, for example, in that, as explained, the switch element 5a is in the switched position III, and the discharge of the humidity sensor element 1 takes place via diodes shielding it against the power supply 4.

Subsequently, parallel charging of the capacitive humidity sensor element 1 and the charge storage device 3 again takes place in a second cycle, before the discharge of the capacitive humidity sensor element 1 alone results again. The voltage $U_L$ applied to this element rises because of the respectively prevented discharge of the charge storage element 3.

Subsequently, these steps are repeated a total of N_$C_S$-times, wherein the charge storage element 3 is charged again and again in the course of successive charge cycles, i.e. the voltage $U_L$ rises in the course of this, until it has reached the comparison voltage $U_V$, or the reference value, as already explained above. Upon reaching the comparison voltage $U_V$, the number $N\_C_S$ of the charging operations performed up to this time is determined in this embodiment of the method in accordance with the invention. Since the number $N\_C_S$ of the performed charging operations is directly proportional to the capacitance $C_S$ of the humidity sensor element 1, it is also possible, with the capacitance $C_L$ known, to directly determine the capacitance $C_S$ of the humidity sensor element 1 from the number of performed charging operations $N\_C_S$.

This operation is performed in accordance with switching technology in that the voltage $U_L$ at the charge storage element 3 is supplied via the input 11.4 of the control unit to a first input of the comparator unit 12, or the comparator in the control unit 10, while the comparison voltage $U_V$=2.5 V is applied at the second input of the comparator unit 12. Accordingly, if after $N\_C_S$ charging operations the voltage $U_L$ at the charge storage element 3 reaches the comparison voltage $U_V$, an appropriate output signal is generated via the comparator unit 12, by which then the actual count $N\_C_S$ in a counting unit (not represented), which counts the number of charging operations performed, is frozen. The counting unit can be integrated into control unit 10 or arranged externally of the control unit 10.

Thus, in principle it would be possible by the explained process to determine the capacitance $C_S$ of the humidity sensor element 1, i.e. from the determination of the number $N\_C_S$ of the charging processes which have taken place until the comparison voltage $U_V$ has been reached alone, it would be possible in principle to determine $C_S$ if, in accordance with the explained process, the humidity sensor element 1 had been regularly charged and discharged parallel with the charge storage element 3. For avoiding the error sources occurring in such a process, together with possibly changing circuit parameters, however, two separate measurements are preferably performed wherein, analogous to the above described process, initially the number $N\_C_{Ref}$ of the charges performed for the reference element 2 is determined and thereafter, as explained, the number of $N\_C_S$ of charging operations performed for the humidity sensor element 1 is determined, until the comparison voltage $U_V$, or the reference value, have been reached.

For the first separate measurement for determining $N\_C_{Ref}$, the reference element 2, instead of the humidity sensor element 3, should be made active by the appropriate actuation of the switch elements 5a, 5b via the outputs 11.1, 11.2. This means that in the charging phase the switch element 5b is closed (switching state I), the switch element 5a is open (switching state II), and the switch element 5c is closed (switching state I), etc.

On the basis of the above mentioned direct proportionality of the number of required charging operations for the appropriate capacitance, it is then possible, with the reference capacitance $C_{Ref}$ known, to have the control unit 10 determine the desired electrical measured value $C_S$ in accordance with the following equation (3):

$$C_S = C_{Ref} * (N\_C_{Ref}/N\_C_S) \quad \text{(Equ. 3)}$$

In case of the example rH=0%, with measured values approximately $N\_C_{Ref}$=4218, $N\_C_S$=4746 and $C_{Ref}$=180 pF, the desired capacitance $C_S$ then correctly results as $C_S$=159.97 pF≈160 pF.

An important advantage of this process can be stated to be that in this way it is possible to achieve a wide-ranging insensitivity to possible changes in the various structural components. Such changes then have equal effects on both separate measurements and do no cause measurement errors in the determination of the capacitance.

Thus, a possible temperature-related change in the capacitance $C_L$ of the charge storage element 3 has no substantial effects on the determination of the capacitance $C_S$. If the capacitance $C_L$ should change, for example because of temperature effects from $C_L$=1000 nF to $C_L$=1100 nF, $N\_C_{Ref}$=4640 and $N\_C_S$=5220 result as measured values, i.e. in accordance with Equ. (3) a determined capacitance $C_S$=160.0 pF for the humidity sensor element 1. The error-caused change in the value determined for $C_s$ lies outside of the resolution limits of the circuit arrangement in accordance with the present invention, and is therefore not critical.

Figure 3:
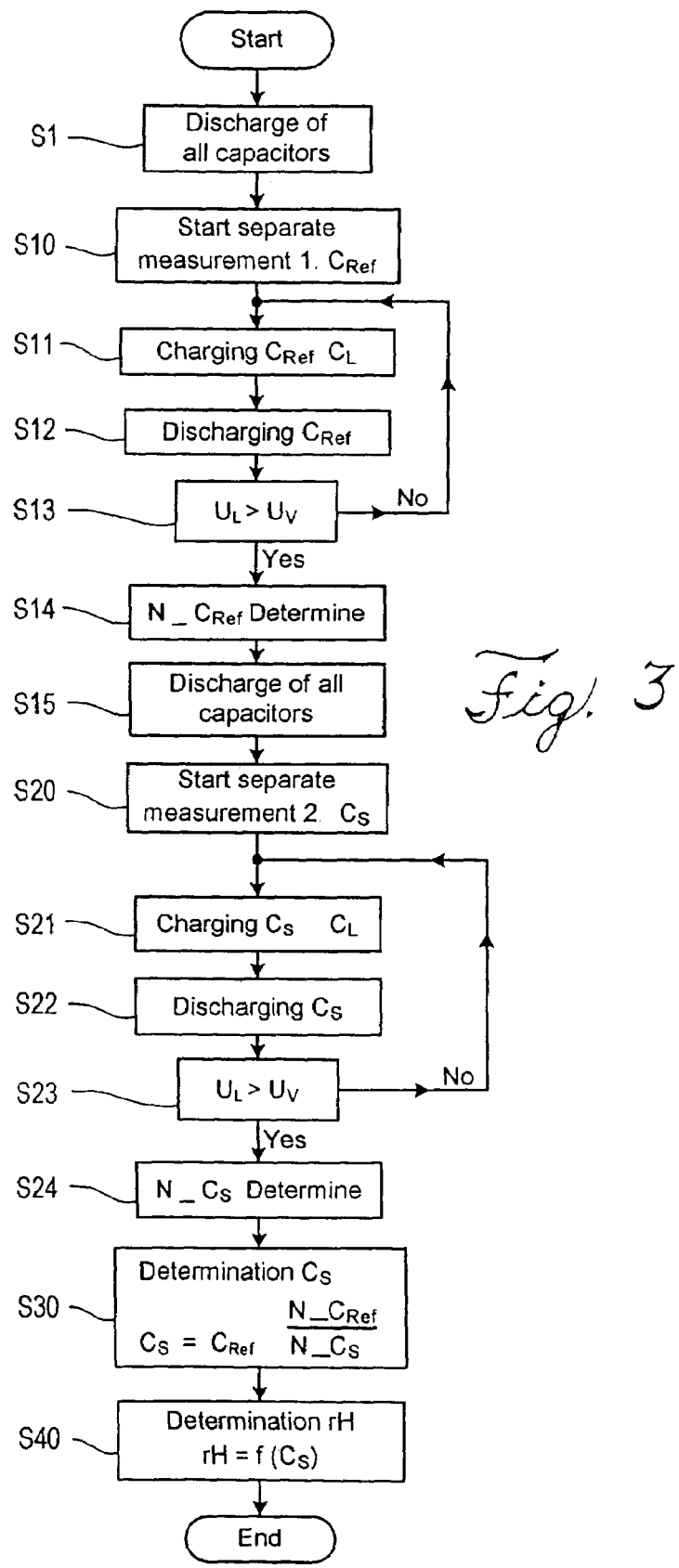
FIG. 3 is a flow diagram for explaining one embodiment of a method in accordance with the present invention.

The way of proceeding within the scope of an advantageous embodiment of the method in accordance with the present invention, by which the relative ambient humidity is determined, is represented again in the form of a flow diagram in FIG. 3.

Following the start of measurements and the discharge of all capacitors in step S1, the first separate measurement begins in step S10, wherein initially the reference element is measured. To this end, charging of the reference element and of the charge storage element, which have the (known) capacitances $C_{Ref}$ and $C_L$, takes place in the first charge/discharge cycle in accordance with method step S11. In method step S11, the reference element of a capacitance $C_{Ref}$ is discharged, while the discharge of the charge storage element is prevented, as explained above. Thereafter a check is made in step S13, whether the charge contained in the charge storage element, or the voltage $U_L$ corresponding to it, has already exceeded a predetermined reference value, or the comparison voltage $U_V$. If this is not the case, a new charge/discharge cycle takes place, etc.; however, if the comparison voltage $U_V$ has been exceeded, the number $N\_C_{Ref}$ of the charge/discharge cycles performed up to this time is determined and recorded in step S14. At the termination of the first separate measurement, or prior to the second separate measurement, a complete discharge of all capacitors in the circuit arrangement, in particular the reference element, the humidity sensor element, as well as the charge storage element, takes place in step S15, in order to produce in this way identical starting conditions in all capacitors, wherein U=0 V.

Subsequently the second separate measurement starts in step S20, in which the humidity sensor element with the humidity-dependent capacitance $C_S$ is measured. Analogously to the previous procedure, the humidity sensor element and the charge storage element are initially charged in step S21, and in step S22 only the humidity sensor element with the capacitance $C_S$ is discharged. In step S23 and analogously to the procedure in the first separate measurement, a check is also performed whether the charge contained in the charge storage element, or the voltage $U_L$ corresponding to this, has already exceeded a predetermined reference value, or the comparison voltage $U_V$. If this is not the case, a fresh charge/discharge cycle takes place, etc.; but if the comparison voltage $U_V$ has been exceeded, the number $N\_C_S$ of the charge/discharge cycles performed up to this time is determined and recorded in step S24.

In method step S30 it is possible to determine the desired measurement value in the form of the capacitance $C_S$ of the humidity sensor element by the above explained Equation (3) from the known capacitance $C_{Ref}$ of the reference element and the two measured values $N\_C_S$, $N\_C_{Ref}$.

Finally, in method step S40, the relative humidity is determined by the control unit 10 in a known manner as a function of the value $C_S$ from the capacity $C_S$ of the humidity sensor element. The relative humidity rH is then available in the respective application for further processing.

The circuit arrangement, or the method, can of course be modified within the scope of the present invention.

It is pointed out that further embodiment variations of the software or hardware of course exist in connection with the circuit arrangement explained by way of example.

It can thus be provided to arrange a resistor in series with the various capacitances in order to limit the charge current of the capacitors in this way.

Furthermore, within the scope of the method in accordance with the present invention it is possible to interchange the sequence of the two separate measurements, i.e. first to measure the humidity sensor element and only then the reference element.

Moreover, alternatively to the explained process it is possible not to determine the number of charge operations performed until the reference value in respect to the comparison voltage $U_V$ has been reached, but instead the time $t_S$ (measuring the humidity sensor element), or $t_{Ref}$ (measuring the reference element), which has passed up to this point. The determination of the relative humidity takes place analogously to the previously described process, wherein then the values $N\_C_{Ref}$ and $N\_C_S$ must be replaced by the values $t_S$ and $t_{Ref}$ in Equ. (3). In this case it is necessary to provide appropriate devices for measuring time in the control unit in place of the above mentioned counting unit.

Further exemplary embodiments exist within the scope of the present invention besides the described examples.

I claim:

1. A circuit arrangement for capacitive humidity measurement, comprising:
   a capacitive element to be measured;
   a plurality of switch elements;
   a charge storage element; and
   a control unit electrically connected to said capacitive element, said plurality of switch elements and said charge storage element, wherein said control unit controls said plurality of switch elements so that a plurality of charging operations and a plurality of discharging operations of said capacitive element are performed, and a parallel charging of said charge storage element are performed without discharging said charge storage element, until said charge storage element has been charged to a defined reference value, and a determination of a capacitance of said capacitive element is performed from a determination of a number of said plurality of charging operations, or of a time until said charge storage element has a charge that reaches said reference value.

2. The circuit arrangement in accordance with claim 1, wherein said charge storage element is a capacitor and, for determining capacitance, is arranged switched in series with said capacitive element.

3. The circuit arrangement in accordance with claim 2, wherein one of said plurality of switch elements is a diode arranged between said charge storage element and said capacitive element in such a way that discharge of said charge storage element is not possible during discharge of said capacitive element.

4. The circuit arrangement in accordance with claim 1, wherein said control unit is a microprocessor, which has a number of definitely programmable inputs and outputs for capacitance measuring, which are connected with said plurality of switch elements and said charge storage element.

5. The circuit arrangement in accordance with claim 1, wherein said control unit comprises a comparator unit with a first input and a second input, and a predetermined comparison voltage is applied at said first input as a reference value, and a voltage picked up at said charge storage element is applied to said second input, so that in case said predetermined comparison voltage is exceeded by said voltage picked up at said charge storage element, a defined output signal of said comparator unit is generated via said voltage picked up at said charge storage element.

6. The circuit arrangement in accordance with claim 5, wherein said control unit further comprises a counting unit which detects a number of charging operations which have taken place until said predetermined comparison voltage is exceeded by said voltage picked up at said charge storage element.

7. A circuit arrangement for capacitive humidity measurement, comprising:
   a capacitive element to be measured;
   a plurality of switch elements;
   a charge storage element;
   a control unit electrically connected to said capacitive element, said plurality of switch elements and said charge storage element, wherein said control unit controls said plurality of switch elements so that a number of charging operations and a number of discharging operations of said capacitive element are performed, as well as a parallel charging of said charge storage element takes place, until said charge storage element has been charged to a defined reference value, and a determination of a capacitance of said capacitive element is performed from a determination of said number of charging operations, or of a time until said reference value is reached; and
   a second capacitive element to be measured, wherein said capacitive element is a capacitive humidity sensor element and said second capacitive element is a capacitive reference element, and wherein said plurality of switch elements selectively serially connect respectively one of said capacitive element and said second capacitive element with said charge storage element and said control unit for determining capacitance.

8. The circuit arrangement in accordance with claim 7, wherein said capacitive reference element has a known capacitance.

9. The circuit arrangement in accordance with claim 8, wherein said control unit determines said capacitance of said humidity sensor element based on said known capacitance and said number of charging operations detected in two separate measurements.

10. The circuit arrangement in accordance with claim 9, wherein said control unit determines a relative ambient humidity based on said determined capacitance of said humidity sensor.

11. The circuit arrangement in accordance with claim 7, wherein said charge storage element is a capacitor and, for determining capacitance, is arranged switched in series with said capacitive element.

12. The circuit arrangement in accordance with claim 11, wherein one of said plurality of switch elements is a diode arranged between said charge storage element and said capacitive element in such a way that discharge of said charge storage element is not possible during discharge of said capacitive element.

13. The circuit arrangement in accordance with claim 7, wherein said control unit is a microprocessor, which has a number of definitely programmable inputs and outputs for capacitance measuring, which are connected with said plurality of switch elements and said charge storage element.

14. The circuit arrangement in accordance with claim 7, wherein said control unit comprises a comparator unit with a first input and a second input, and a predetermined comparison voltage is applied at said first input as a reference value, and a voltage picked up at said charge storage element is applied to said second input, so that in case said predetermined comparison voltage is exceeded by said voltage picked up at said charge storage element, a defined output signal of said comparator unit is generated via said voltage picked up at said charge storage element.

15. The circuit arrangement in accordance with claim 14, wherein said control unit further comprises a counting unit which detects a number of charging operations which have taken place until said predetermined comparison voltage is exceeded by said voltage picked up at said charge storage element.

16. A method for operating a circuit arrangement for capacitive humidity measurement, which is comprised of a capacitive element, a plurality of switch elements, a charge storage element and a control unit, the method comprising:
performing a plurality of charging and discharging operations of said capacitive element via said plurality of switch elements and said control unit;
performing parallel charging of said charge storage element via said plurality of switch elements and said control unit, wherein said charging and discharging of said capacitive element and said parallel charging are performed without discharging said charge storage element until said charge storage element has been charged to a defined reference value; and
performing a definition of a capacitance of said capacitive element by determining either a number of charging operations, or a time until said charge storage element has a charge that reaches said reference value.

17. The method in accordance with claim 16, further comprising preventing a discharge of said charge storage element during a discharge of said capacitive element.

18. The method in accordance with claim 16, wherein said control unit is a microprocessor, which has a number of definitely programmable inputs and outputs for capacitance measuring, which are connected with said plurality of switch elements and said charge storage element.

19. The method in accordance with claim 16, wherein for determining said number of charging operations or said time until said reference value is reached, said control unit comprises a comparator unit with a first input and a second input, and a predetermined comparison voltage is applied at said first input as a reference value, and a voltage picked up at said charge storage element is applied to said second input, so that in case said predetermined comparison voltage is exceeded by said voltage picked up at said charge storage element, said number of charging operations performed up to this moment, or said time until said reference value is reached, is determined.

20. A method for operating a circuit arrangement for capacitive humidity measurement, which is comprised of a capacitive element, a plurality of switch elements, a charge storage element and a control unit, the method comprising:
performing charging and discharging of said capacitive element via said plurality of switch elements and said control unit;
performing parallel charging of said charge storage element via said plurality of switch elements and said control unit, wherein said charging and discharging of said capacitive element and said parallel charging are performed until said charge storage element has been charged to a defined reference value; and
performing a definition of a capacitance of said capacitive element by determining either a number of charging operations, or a time until said reference value is reached,
wherein said circuit arrangement further comprising a second capacitive element to be measured, wherein said capacitive element is a capacitive humidity sensor element and said second capacitive element is a capacitive reference element, and wherein said plurality of switch elements selectively connect respectively one of said capacitive element and said second capacitive element with said charge storage element and said control unit for determining capacitance.

21. The method in accordance with claim 20, further comprising:
determining a first value of said number of charging operation or said time until reaching said reference value via said reference element;
determining a second value of said number of charging operation or said time until reaching said reference value via said humidity sensor element; and
determining a capacitance of said humidity sensor element from 1) said first and second values of said number of charging operations, or from said first and second values of said times until said reference value is reached, and 2) a known capacitance of said reference element.

22. The method in accordance with claim 21, wherein determining of said capacitance of said humidity sensor element is determined in accordance with the following equation:

$$C_S = C_{Ref} * (N\_C_{Ref}/N\_C_S)$$

wherein
$C_S$=said capacitance of the humidity sensor element,
$C_{Ref}$=said known capacitance of the reference element,
$N\_C_{Ref}$=the number of charging operations during said determining via said reference element,
$N\_C_S$=the number of charging operations during said determining via said humidity sensor element.

23. The method in accordance with claim 21, wherein said reference element, said humidity sensor element and said charge storage element are completely discharged between determining via said reference element and said determining via said humidity sensor element.

24. The method in accordance with claim 21, further comprising determining a relative ambient humidity from said capacitance of said humidity sensor element.

25. The method in accordance with claim 20, further comprising preventing a discharge of said charge storage element during a discharge of said capacitive element.

26. The method in accordance with claim 20, wherein said control unit is a microprocessor, which has a number of definitely programmable inputs and outputs for capacitance measuring, which are connected with said plurality of switch elements and said charge storage element.

27. The method in accordance with claim 20, wherein for determining said number of charging operations or said time until said reference value is reached, said control unit comprises a comparator unit with a first input and a second input, and a predetermined comparison voltage is applied at said first input as a reference value, and a voltage picked up at said charge storage element is applied to said second input, so that in case said predetermined comparison voltage is exceeded by said voltage picked up at said charge storage element, said number of charging operations performed up to this moment, or said time until said reference value is reached, is determined.

28. A method for operating a circuit arrangement for capacitive humidity measurement, which is comprised of a capacitive element, a plurality of switch elements, a charge storage element and a control unit, the method comprising:
performing charging and discharging of said capacitive element via said plurality of switch elements and said control unit;
performing parallel charging of said charge storage element via said plurality of switch elements and said control unit, wherein said charging and discharging of said capacitive element and said parallel charging are performed until said charge storage element has been charged to a defined reference value;
performing a definition of a capacitance of said capacitive element by determining either a number of charging operations, or a time until said reference value is reached;
a) charging said capacitive element with a first defined charge;
b) charging said charge storage element with a second defined charge;
c) discharging charge from said capacitive element while said second defined charge stored in said charge storage element remains unchanged;
d) repeating steps a)–c) until a total amount of charge stored in said charge storage element has reached a predetermined reference value; and
e) determining a number of the charging operations b) that occur to reach said reference value, or a time until said reference value is reached; and
f) determining said capacitance from said determined number of charging operations or said time until said reference value is reached.

29. The method in accordance with claim 28, wherein said circuit arrangement further comprising a second capacitive element to be measured, wherein said capacitive element is a capacitive humidity sensor element and said second capacitive element is a capacitive reference element, and wherein said plurality of switch elements selectively connect respectively one of said capacitive element and said second capacitive element with said charge storage element and said control unit for determining capacitance.

30. The method in accordance with claim 29, further comprising:
determining a first value of said number of charging operation or said time until reaching said reference value via said reference element;
determining a second value of said number of charging operation or said time until reaching said reference value via said humidity sensor element; and
determining a capacitance of said humidity sensor element from 1) said first and second values of said number of charging operations, or from said first and second values of said times until said reference value is reached, and 2) a known capacitance of said reference element.

31. The method in accordance with claim 30, wherein determining of said capacitance of said humidity sensor element is determined in accordance with the following equation:

$$C_S = C_{Ref} * (N\_C_{Ref}/N\_C_S)$$

wherein
$C_S$=said capacitance of the humidity sensor element,
$C_{Ref}$=said known capacitance of the reference element,
$N\_C_{Ref}$=the number of charging operations during said determining via said reference element,
$N\_C_S$=the number of charging operations during said determining via said humidity sensor element.

32. The method in accordance with claim 28, wherein said control unit is a microprocessor, which has a number of definitely programmable inputs and outputs for capacitance measuring, which are connected with said plurality of switch elements and said charge storage element.

33. The method in accordance with claim 28, wherein for determining said number of charging operations or said time until said reference value is reached, said control unit comprises a comparator unit with a first input and a second input, and a predetermined comparison voltage is applied at said first input as a reference value, and a voltage picked up at said charge storage element is applied to said second input, so that in case said predetermined comparison voltage is exceeded by said voltage picked up at said charge storage element, said number of charging operations performed up to this moment, or said time until said reference value is reached, is determined.

34. The method in accordance with claim 33, wherein said reference element, said humidity sensor element and said charge storage element are completely discharged between determining via said reference element and said determining via said humidity sensor element.

35. The method in accordance with claim 33, further comprising determining a relative ambient humidity from said capacitance of said humidity sensor element.

* * * * *